US00PP37014P2

(12) United States Plant Patent
Qiu

(10) Patent No.: US PP37,014 P2
(45) Date of Patent: Oct. 14, 2025

(54) GRAPEVINE PLANT NAMED 'Norton Blanc'

(50) Latin Name: *Vitis vinifera*
Varietal Denomination: Norton Blanc

(71) Applicant: MISSOURI STATE UNIVERSITY, Springfield, MO (US)

(72) Inventor: Wenping Qiu, Springfield, MO (US)

(73) Assignee: MISSOURI STATE UNIVERSITY, Springfield, MO (US)

( * ) Notice: Subject to any disclaimer, the term of this patent is extended or adjusted under 35 U.S.C. 154(b) by 0 days.

(21) Appl. No.: 18/904,789

(22) Filed: Oct. 2, 2024

(51) Int. Cl.
*A01H 6/88* (2018.01)
*A01H 5/08* (2018.01)

(52) U.S. Cl.
USPC ..... Plt./207

(58) Field of Classification Search
USPC ..... Plt./207
CPC ..... A01H 6/88; A01H 5/08
See application file for complete search history.

*Primary Examiner* — Keith O. Robinson
(74) *Attorney, Agent, or Firm* — Kutak Rock LLP; Brian L. Main; Ryan Hinderliter

(57) ABSTRACT

A new and distinct grapevine cultivar named 'Norton Blanc' is provided. 'Norton Blanc' was produced from a cross between 'Norton' and 'Cabernet Sauvignon' grapevines. 'Norton Blanc' produces a white berry that in turn is used to produce a unique and excellent white wine. 'Norton Blanc' is distinguished by its production volume and consistency under the climate and soil conditions in the Midwest region of the United States, disease resistance, cold hardiness, and unique berry chemistry, among other characteristics.

7 Drawing Sheets

Latin name of genus and species: *Vitis vinifera.*
Varietal denomination: 'Norton Blanc'.

BACKGROUND OF THE INVENTION

The present cultivar originated from a cross of 'Norton' (female) (not patented) and 'Cabernet Sauvignon' (male) (not patented) grapevines made in May 2005. Anthers were removed from 'Norton' grapevine's flowers, and pollen was collected from 'Cabernet Sauvignon' grapevine. The 'Cabernet Sauvignon' pollen was shed onto stigmas of 'Norton' grapevine flowers by gentle brushing. A paper bag was wrapped around pollinated 'Norton' flowers for one week and then removed to expose the formed berries.

In October 2005, 300 seeds were harvested from berries that developed from the aforementioned pollinated flowers. In March 2006, seedlings were germinated in a greenhouse, and in June 2006, 100 seedlings were planted in a vineyard at the Missouri State Fruit Experiment Station in Mountain Grove, Missouri.

From 2007-2011, viticultural traits of the 100 seedlings were evaluated. Seven new grape varieties, including 'Norton Blanc', were selected and planted at the Missouri State Fruit Experiment Station for further evaluation in June 2011.

From 2015 to 2020, 12 'Norton Blanc' grapevines were evaluated at the Missouri State Fruit Experiment Station in Mountain Grove, Missouri, with 12 'Norton' grapevines and 12 'Cabernet Sauvignon' grapevines, the two parental cultivars, and six other selections, all grown in the same vineyard for comparison purposes. Since then, additional 'Norton Blanc' vines have been propagated, grown, and further evaluated for viticultural and enological traits.

In 2016, a first vintage white wine was made from 'Norton Blanc' grapes that were planted in 2011.

SUMMARY OF THE INVENTION

The present invention is a new and distinct variety of grapevine named 'Norton Blanc' produced from a cross of 'Norton' and 'Cabernet Sauvignon' grapevines. Although 'Norton' and 'Cabernet Sauvignon' are each red wine grape cultivars, 'Norton Blanc' is a white grape variety.

The fruit clusters of 'Norton Blanc' are small, but not extremely tight, and the berries are slightly larger than the berries of both 'Norton' and 'Cabernet Sauvignon' grapevines.

Bud break of 'Norton Blanc' is late compared to currently grown wine grape cultivars in Missouri, including 'Cabernet Sauvignon', and on average is four days later than bud break of 'Norton' grapevines. Observed bud break dates of existing 'Norton Blanc' grapevines in Missouri range from April 11th to May 4th. For the same 'Norton Blanc' grapevines, observed flowering occurred around June 6th, and observed veraison occurred around August 12th.

Harvest of existing 'Norton Blanc' grapevines in Missouri has been between September 20th and October 9th. This is slightly earlier than harvests for 'Norton' and 'Cabernet Sauvignon' in the same region, which is from September 27th to October 15$^{th}$, but later than harvests for most white grape cultivars. At harvest, pH values of 'Norton Blanc' are consistently around 3.35, while the pH of 'Norton' is around 3.39. Titratable acidity of 'Norton Blanc' ranges from 0.57 to 0.66 g/100 mL, which is lower than the average of 0.72 g/100 mL for 'Norton'.

Sugar content of 'Norton Blanc' ranges from 20.3 Brix to 25.2 Brix, depending on the season. In most years, the sugar content of 'Norton Blanc' has been two degrees Brix lower than the sugar content of 'Norton', but higher than the sugar content of 'Cabernet Sauvignon';.

Over the years, yield per vine of 'Norton Blanc' has been very consistent, with the lowest yield being 11.2 lbs. per vine, the highest being 13.2 lbs. per vine, and the average being 12.35 lbs. per vine. 'Norton' had larger fluctuations in yield during these years, with an average of 14 lbs. per vine. 'Norton Blanc' is very cold-hardy in comparison with 'Cabernet Sauvignon'.

When grown using a standard spray program in Missouri, all common grape diseases, including pre-harvest soft rot (*Pectobacterium carotovorum*, which was previously known as *Erwinia carotovora*), were well controlled. 'Norton Blanc' is moderately resistant to downy mildew (*Plasmopara viticola*) and bunch rot (*Botrytis cinerea*) based on laboratory and vineyard evaluation. Further, 'Norton Blanc' survived late spring freezes in 2020 and in 2021. Additionally, 'Norton Blanc' is easily propagated from dormant wood cuttings, at about a 90% rooting percentage.

Wine produced from 'Norton Blanc' berries has an aroma of fresh spring grass or fresh-cut lime. The wine palate has a touch of green apricot, plum, or apple. The wine is light-bodied with a complex structure of balanced acidity. The wine is crisp, clear, clean, and sharp. Wine from 'Norton Blanc' is a new, unique style of wine as compared to traditional white wines.

'Norton Blanc' grapevine can be grown utilizing standard viticultural management practices, with no special techniques required. 'Norton Blanc' grows well for commercial production under the climate and soil conditions in the Midwest region of the United States.

BRIEF DESCRIPTION OF THE PHOTOGRAPHS

The accompanying photographs show typical specimens of the new cultivar in color as nearly true as it is reasonably possible to make in a color illustration of this character.

DETAILED BOTANICAL DESCRIPTION

Figure 1:
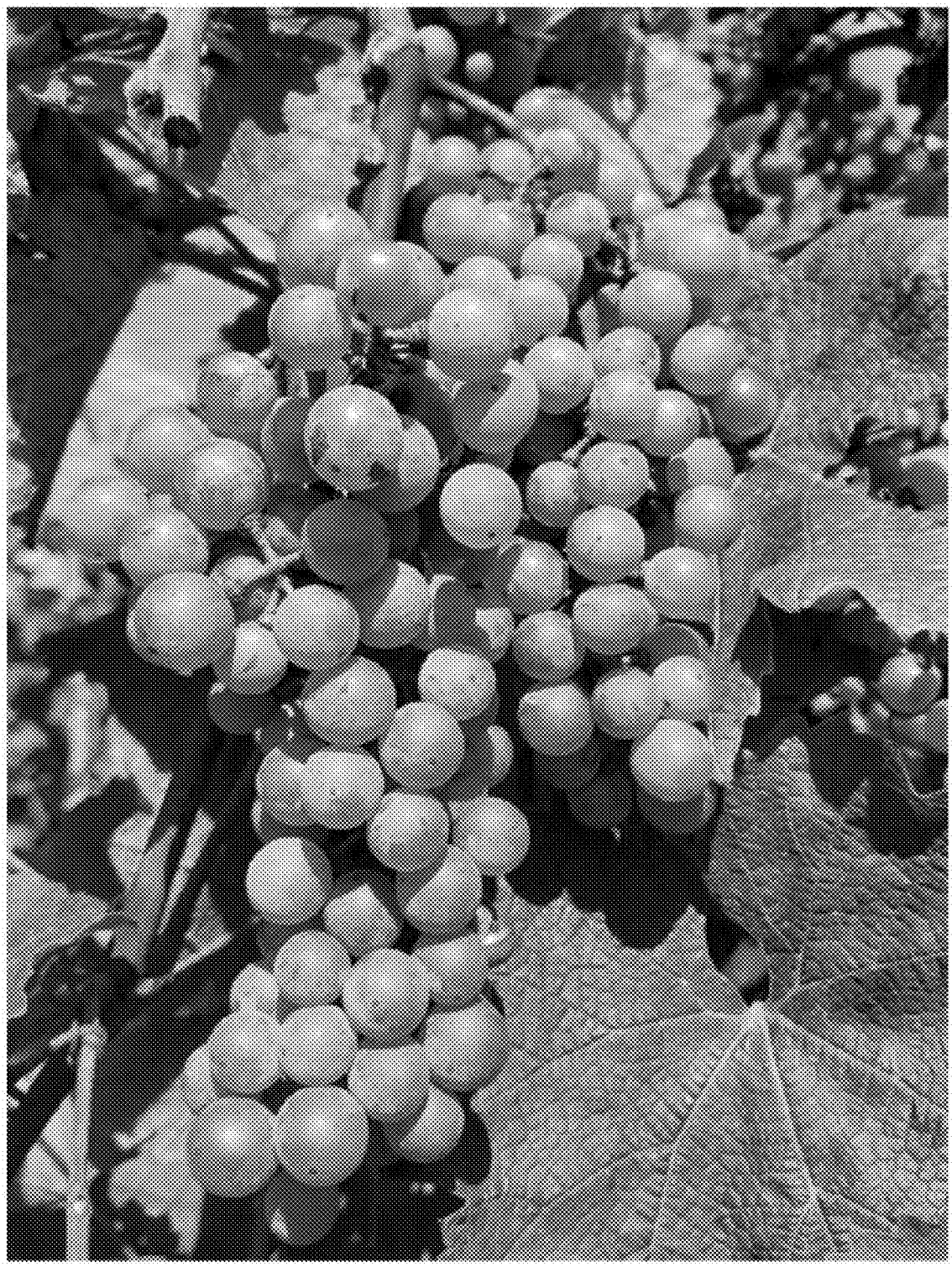
FIG. 1 is a photograph showing a typical cluster of healthy fruit of 'Norton Blanc' on a 10-year-old vine at the Missouri State Fruit Experiment Station, Mountain Grove, Missouri.
Figure 2:
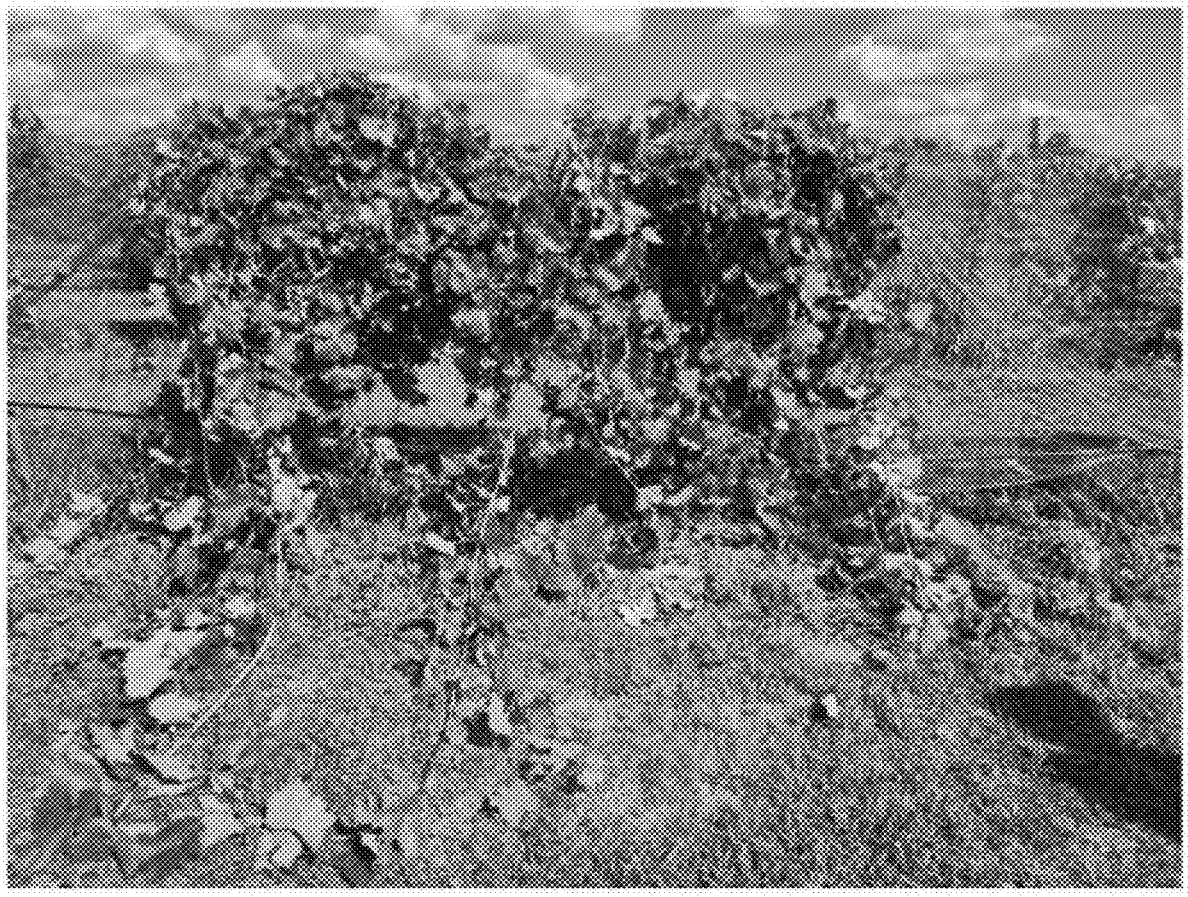
FIG. 2 is a photograph showing a 12 year-old 'Norton Blanc' grapevine.
Figure 3:
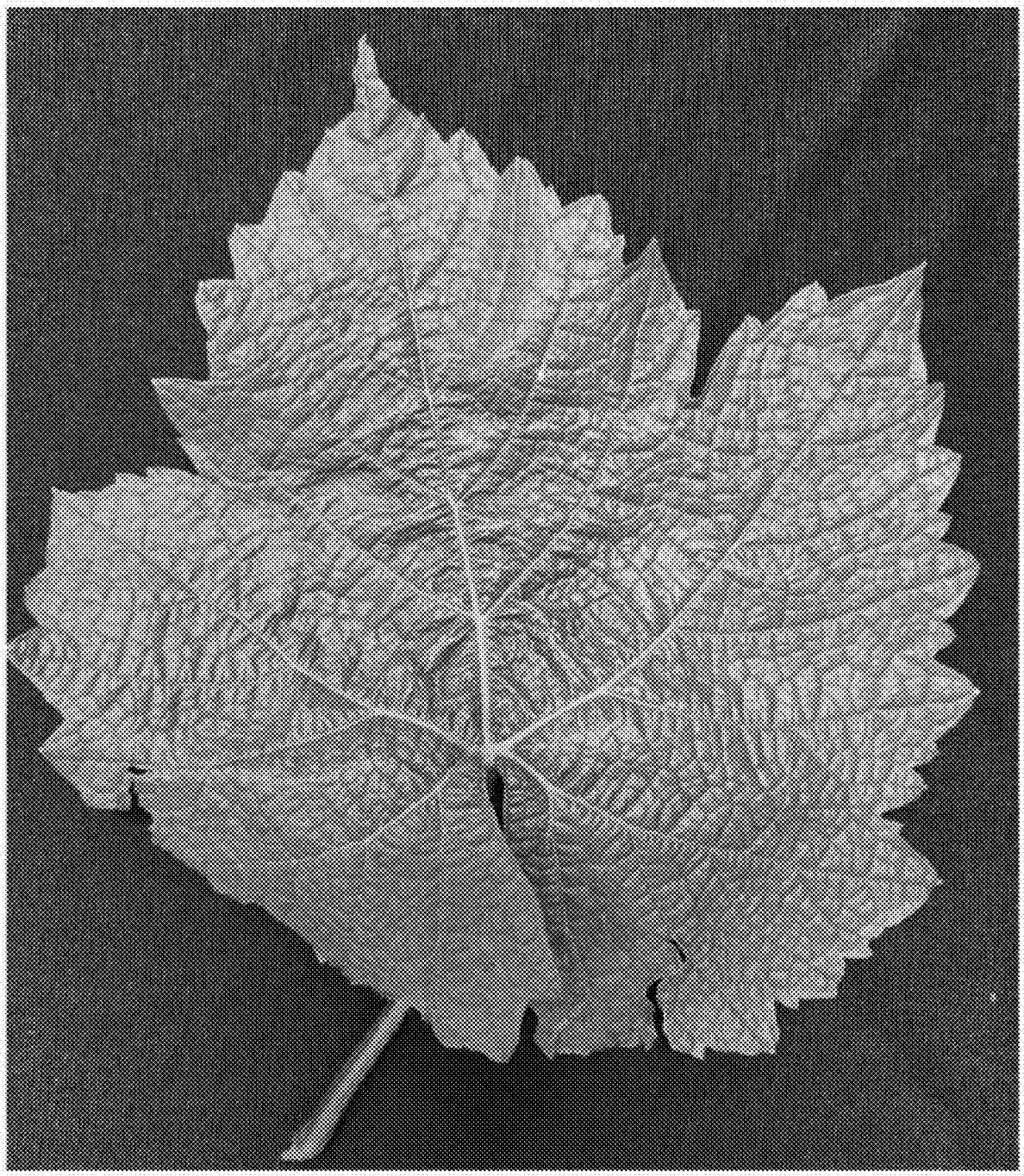
FIG. 3 is a photograph showing a front view of a 'Norton Blanc' leaf.
Figure 4:
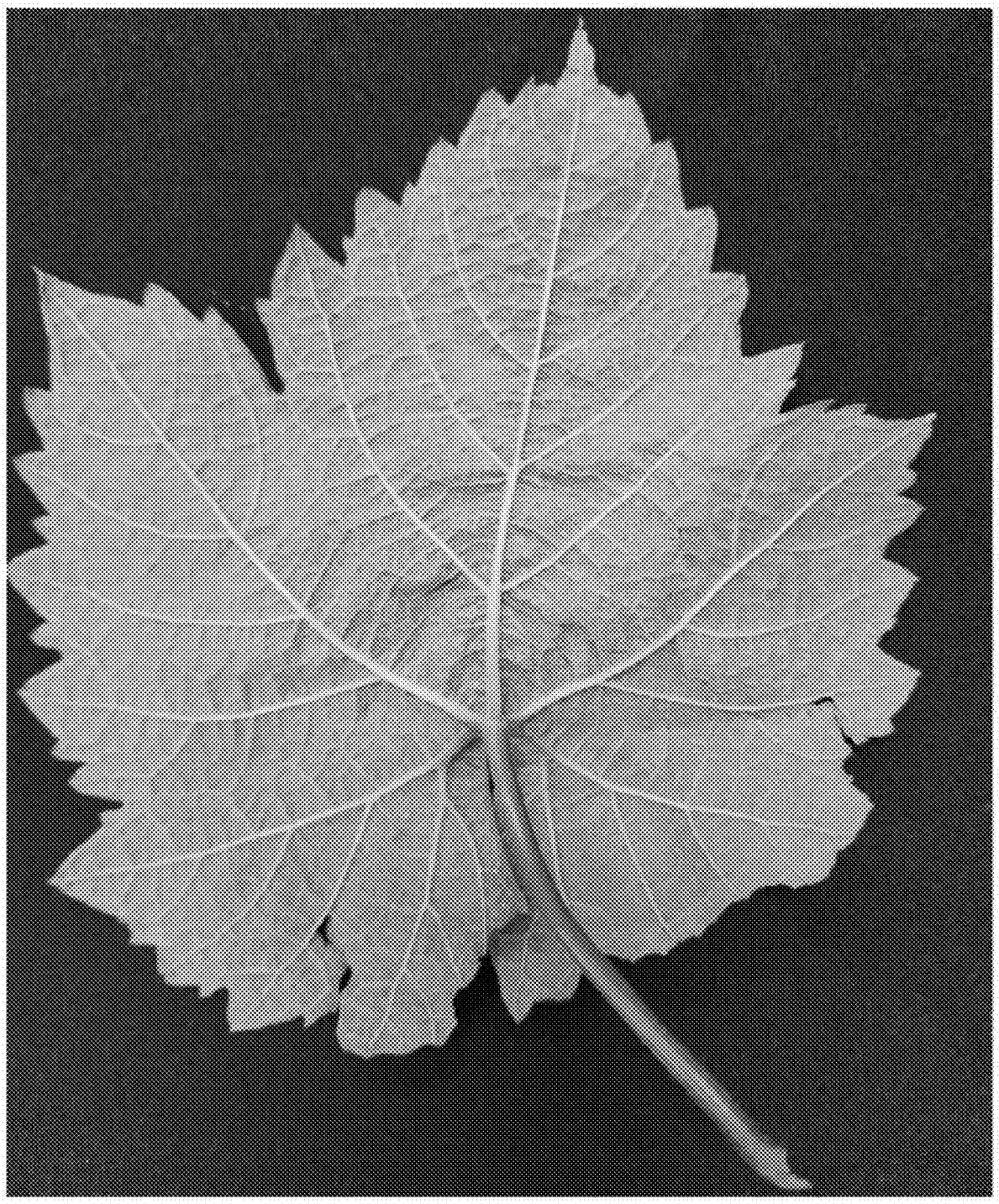
FIG. 4 is a photograph showing a rear view of a 'Norton Blanc' leaf.
Figure 5:
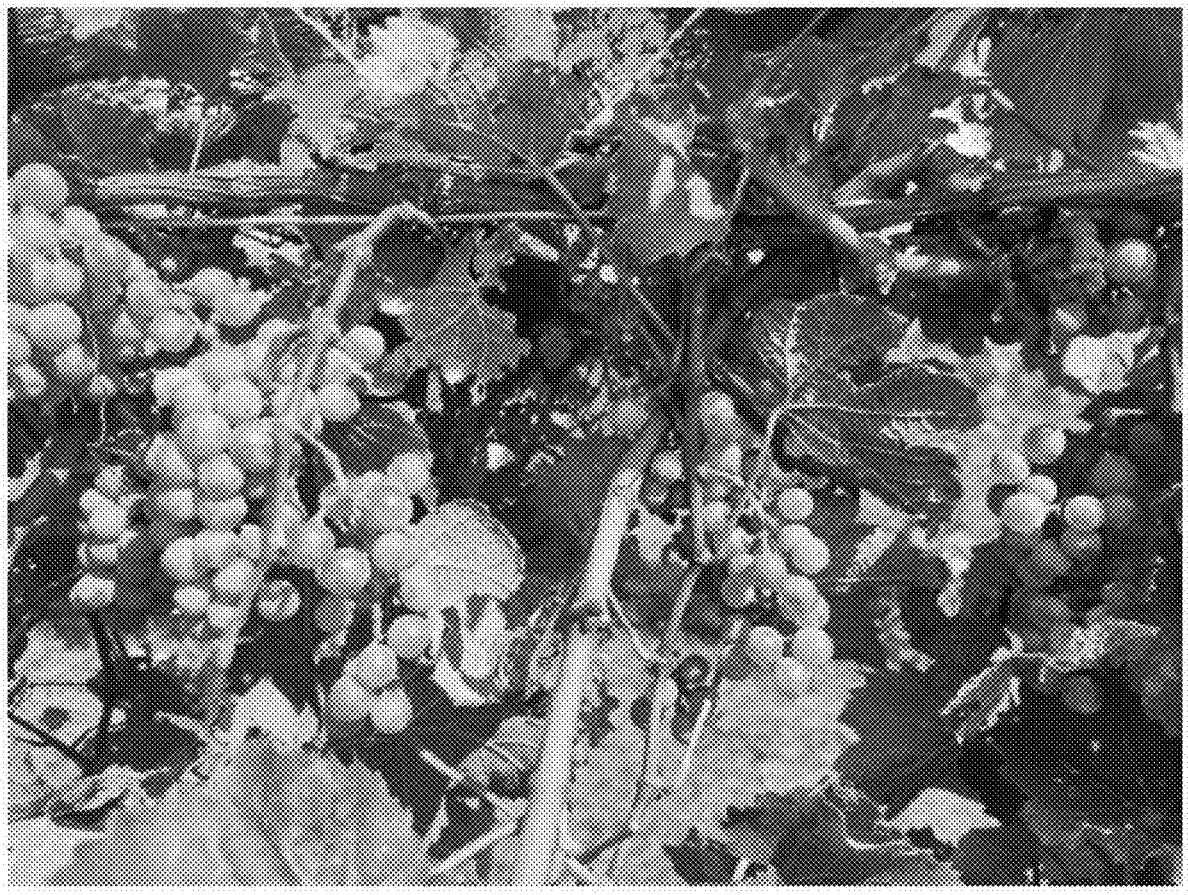
FIG. 5 is a photograph of a mature fruit bunch from 'Norton Blanc' grapevine.
Figure 6:
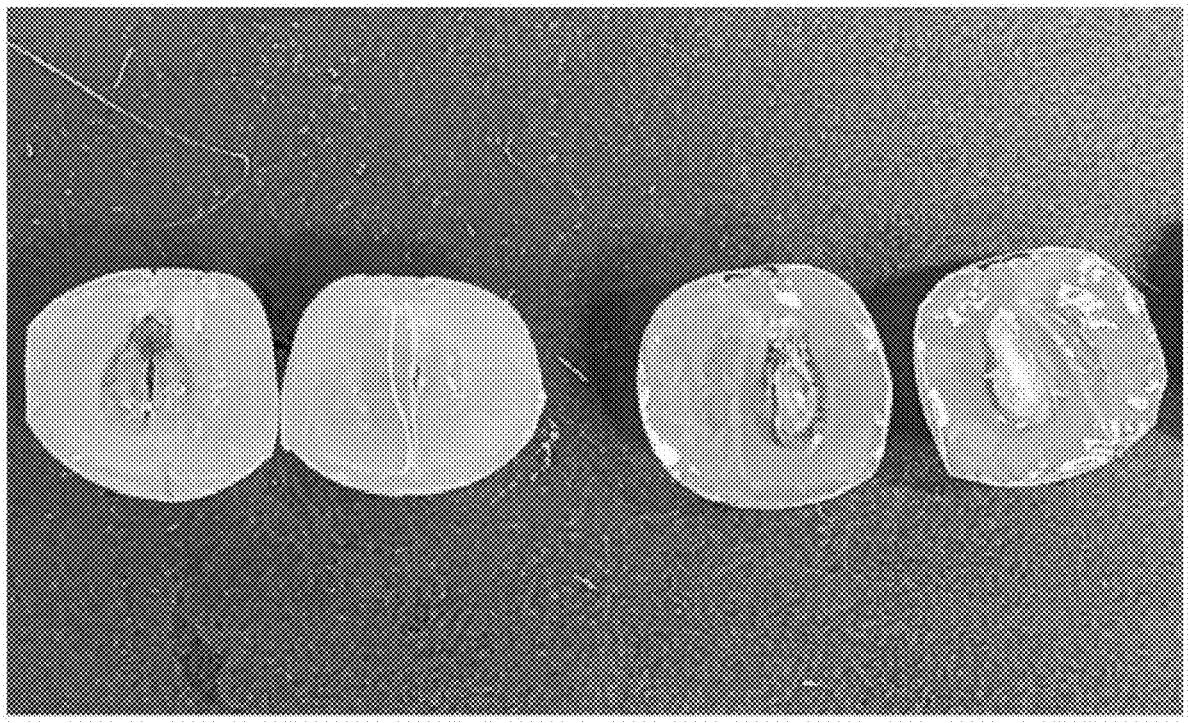
FIG. 6 is a photograph showing cross-sectional views of 'Norton Blanc' berries.
Figure 7:
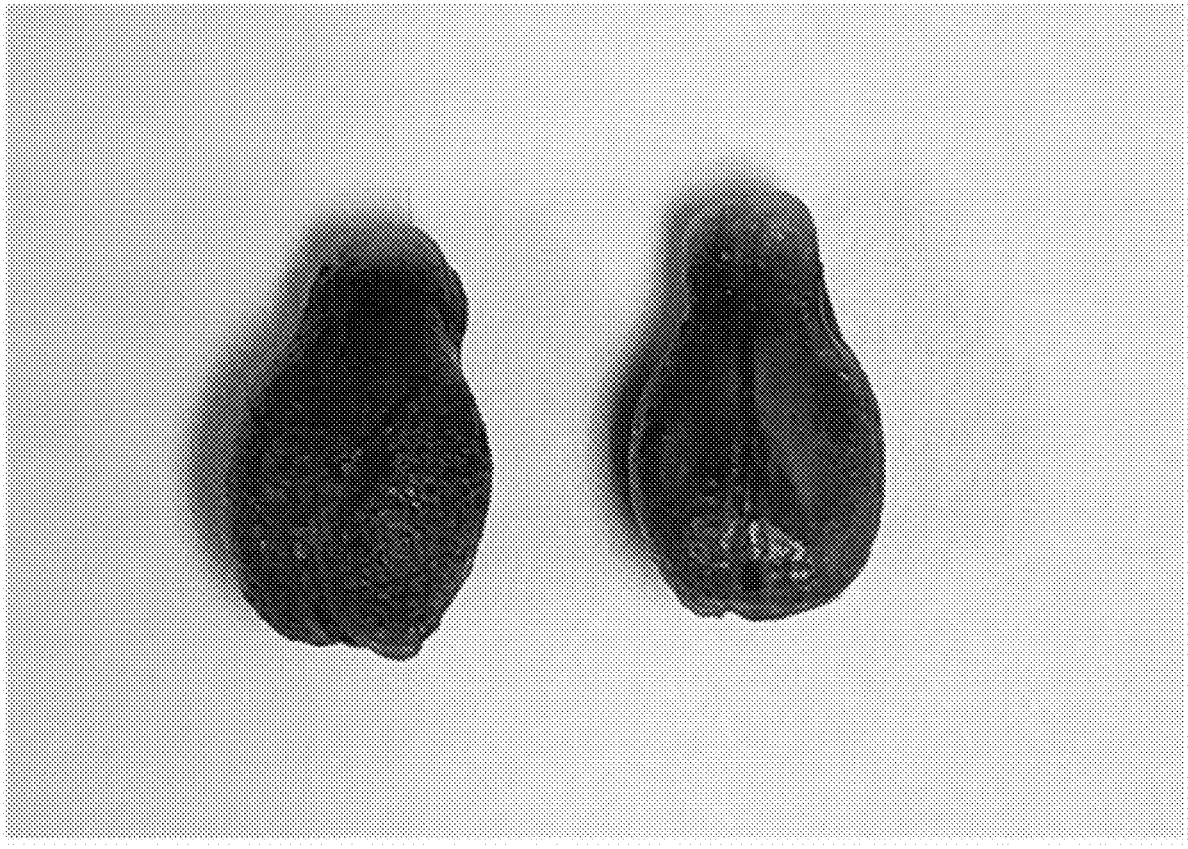
FIG. 7 is a photograph showing an enlarged view of 'Norton Blanc' seeds.

The following descriptions of 'Norton Blanc' apply to grapevines planted in Mountain Grove, Missouri in 2015. When dimensions, sizes, colors, or other characteristics are provided herein, it is to be understood that such characteristics are approximations set forth as accurately as possible. Variations based on climatic conditions, fertilization, pruning, pest control, and other cultural practices and factors that impact the exact exhibition of certain specific characteristics are to be expected. Color codes used are those of The Royal Horticultural Society Colour Chart (*Royal Horticultural Society.* 1966. R.H.S. Colour Chart. London), and Galet's "A practical ampelography" (P. Galet: "A practical ampelography." 1979, 248 pp. ISBN (Hardback): 978-0-8014-1240-0; CABI Record Number: 19790379291, Publisher: Cornell University Press, Ithaca. USA) was used to describe characteristics of 'Norton Blanc', except where general terms of ordinary dictionary meaning are used.

Vine:

*Size*.—Three 12 year old Norton Blanc vines were measured and averaged at the end of their flowering stage. The average height was 123 inches and the average width was 90 inches. The vines were grown with a two wire trellis (at 22 inches and 68 inches) and they were spaced 8 feet apart with a double cordon.

*Growth vigor*.—High.

*Density of foliage*.—High.

*Productivity*.—Medium, with an average of 12.35 pounds per vine.

Shoots

*Color*.—Green (RHS 144A) turning reddish brown by June (RHS 183A).

*Shoot attitude*.—Upright.

*Openness of shoot tip*.—Closed, flattened shoot tip, reddish edge (RHS 50B).

*Prostrate hairs on young shoot tip*.—Downy white hairs (RHS 159B), with prostate hairs on the tip of the shoot being very sparse to medium.

*Indument of shoot*.—Cobwebby white hairs (RHS 159B).

Trunk:

*Trunk surface texture*.—Rough and peeling in strips.

*Bark color*.—Outer bark (RHS 201A).

*Trunk circumference*.—12.4 cm.

*Trunk straps*.—Peeling bark.

Canes:

*Size/thickness*.—Diameter 0.75 cm.

*Surface texture*.—Glabrous, ridged.

*Color*.—Light brown (RHS 165C) with dark brown freckles (RHS 165A to 165B).

*Shape*.—Round.

*Internode length*.—8.42 cm.

Tendrils:

*Length*.—15.8 cm.

*Diameter*.—1.7 mm.

*Distribution*.—Every node.

*Form*.—Forked.

*Color*.—Greenish yellow (RHS 145A) to reddish brown (RHS 176A).

Buds:

*Number of buds on single-season cane*.—42 nodes on a single season shoot.

*Dimensions of dormant buds*.—Diameter of 0.37 cm.

*Shape of dormant buds*.—Rounded with a point on top.

*Color of dormant buds*.—Pinkish tan (RHS 176C).

*Texture of dormant buds*.—Velvety.

*Bud break*.—Late, between April 11 and May 4.

Leaves:

*General description*.—Leaves orbicular, medium, dark green (RHS 146A, 146B), average to wide convex toothed margin, pubescent below, petiolar sinus with overlapping edges, deep superior sinus, shallow to no inferior sinus.

*Average leaf length*.—16.2 cm.

*Average leaf width*.—15.5 cm.

*Apex of leaf*.—Toothed, coming to a sharp point at the tip of the leaf.

*Base of leaf*.—Deep overlapping lobes (five lobes) cover the petiole.

*Shape of upper lateral leaf sinus*.—Wedge to teardrop shaped.
*Leaf margins*.—Toothed.
*Size of blade*.—251 $cm^2$.
*Shape*.—Orbicular.
*Shape of teeth along leaf margins*.—Convex.
*Length of teeth along leaf margins*.—Average of 6.5 mm.
*General shape of petiole sinus*.—Teardrop shaped.
*Surface texture*.—Bullate.
*Color of upper leaf veins*.—(RHS 149D).
*Color of lower leaf veins*.—(RHS 145C).
*Surface appearance*.—Slightly bullate.
*Length of petiole*.—7.7 cm.
*Petiole thickness*.—4 mm.
*Petiole shape*.—Cylindrical, tapering slightly as it approaches the leaf.
*Petiole color*.—(RHS 177A).
*Length of petiole compared to mid vein*.—7.7 cm compared to 11.9 cm (65%).

Floral cluster:
*Bloom timing*.—May 26 to June 6.
*Cluster form*.—Cylindrical.
*Clusters per shoot*.—Three.
*Cluster length*.—6 cm.
*Cluster width*.—2 cm.
*Cluster peduncles*.—1.75 cm length.
*Cluster peduncle color*.—(RHS 176A).
*Inflorescence*.—Cylindrical, green (RHS 149B), long cluster becoming cream color when calyptra falls.
*Floral stamens*.—Five.
*Flower length*.—5 mm.
*Flower diameter*.—5 mm.
*Flower petals*.—Calyptra begins green (RHS 149B) turns brownish (RHS 173C) and releases.
*Sepals*.—Five.
*Pollen color*.—Cream (RHS 10D) to light yellow (RHS 10A).
*Calyptras separation from flower base*.—Yes.
*Duration of bloom*.—One week.

Fruit:
*Veraison*.—Mid-August.
*Date of maturity*.—Mid-September.
*Bunch size*.—96 berries.
*Bunch length*.—13 cm.
*Bunch width*.—6 cm.
*Bunch form*.—Cylindrical with occasional one shoulder.
*Bunch weight*.—99.3 g.
*Bunch density*.—Moderately compact to loose.
*Peduncle length*.—2.8 cm.
*Peduncle color*.—(RHS 146D).
*Peduncle thickness*.—3 mm.
*Berry form*.—Round.
*Cross sectional view berry form*.—Circular.
*Berry size*.—13.7 mm at equator.
*Berry weight*.—136 g per 100 berries.
*Berry uniformity*.—Uniform.
*Berry pedicel color*.—(RHS 144B).
*Berry pedicel length*.—1 cm.
*Berry pedicel thickness*.—2 mm.
*Attachment*.—Separation from pedicel fairly difficult.
*Berry skin color*.—(RHS 148A).
*Berry skin thickness*.—≤1 mm.
*Berry skin surface texture*.—Smooth.
*Berry skin tenacity to flesh*.—Peels easily.
*Berry skin tendency to crack*.—Slight to none.
*Berry skin reticulation*.—Smooth skin with faint longitudinal white striping (RHS NN155B).
*Berry flesh color*.—(RHS 147A to 146D).
*Juiciness of flesh*.—Moderate.
*Berry firmness*.—Firm.
*Berry juice*.—Clear.
*Solids-sugar percentage at maturity*.—Between 20.3 and 25.2 Brix.
*pH of berry juice*.—3.35.
*Titratable acidity*.—Between 0.57 g/100 mL and 0.66 g/100 mL.
*Yield*.—Average yield of 12.35 lbs. per vine; low yield of 11.2 lbs. per vine; high yield of 13.2 lbs. per vine.
*Seed*.—One to four fully developed seeds present.
*Seed weight*.—490 mg per 10 seeds.
*Seed length*.—6.8 mm.
*Seed width*.—4.5 mm.
*Flavor*.—Sweet tart, with hints of apple peel, mandarin orange, and grass.
*Flavor of resulting wine*.—Palate has touch of green apricot, plum, and apple. Unique, light-bodied wine with complex structure of balanced acidity which is crisp, clear, clean, and sharp.
*Aroma*.—Fresh spring grass and fresh-cut lime.

Having thus described the invention, what is claimed as new and desired to be secured by Letters Patent is:

1. A new and distinct cultivar of grapevine plant named 'Norton Blanc' is substantially illustrated and described herein.

* * * * *